United States Patent [19]

Koleske et al.

[11] Patent Number: 5,268,489

[45] Date of Patent: Dec. 7, 1993

[54] PRODUCTION OF UNSATURATED CYCLOALIPHATIC ESTERS AND DERIVATIVES THEREOF

[75] Inventors: Joseph V. Koleske, Charleston; John N. Argyropoulos, Scott Depot; Oliver W. Smith, Charleston, all of W. Va.

[73] Assignee: Union Carbide Chemicals & Plastics Technology Corporation, Danbury, Conn.

[21] Appl. No.: 14,338

[22] Filed: Feb. 5, 1993

Related U.S. Application Data

[62] Division of Ser. No. 921,311, Jul. 28, 1992, which is a division of Ser. No. 721,799, Jun. 26, 1991, abandoned.

[51] Int. Cl.$^5$ .................. C07D 301/12; C07D 301/16; C07D 303/08; C07D 303/12
[52] U.S. Cl. .................................. 549/215; 549/524; 549/525; 549/526; 549/529; 549/531; 549/544; 549/545; 560/120; 560/125; 560/128
[58] Field of Search ............... 549/525, 544, 545, 524, 549/526, 527, 531, 215; 560/117, 120, 128, 125

[56] References Cited

U.S. PATENT DOCUMENTS

| | | | |
|---|---|---|---|
| 1,944,732 | 1/1934 | Diels et al. | 260/136 |
| 2,716,123 | 8/1955 | Frostick et al. | 260/348 |
| 2,745,847 | 5/1956 | Phillips et al. | 260/348 |
| 2,750,395 | 6/1956 | Phillips et al. | 260/348 |
| 2,794,812 | 6/1957 | Phillips et al. | 260/348 |
| 3,390,169 | 6/1968 | Inukai et al. | 260/468 |
| 3,979,338 | 9/1976 | Sundt | 549/544 |
| 4,100,046 | 7/1978 | Hodakowski et al. | 204/159.23 |
| 4,721,798 | 1/1988 | Mulder | 549/544 |

FOREIGN PATENT DOCUMENTS

| | | | |
|---|---|---|---|
| 662599 | 5/1963 | Canada | 549/525 |
| 752874 | 2/1967 | Canada | 549/545 |
| 2093 | 1/1971 | Japan | 549/545 |
| 1-197460 | 8/1989 | Japan | 560/120 |
| 478001 | 10/1973 | U.S.S.R. | 549/545 |
| 788123 | 12/1957 | United Kingdom | 549/545 |
| 1076304 | 7/1967 | United Kingdom | 560/128 |

OTHER PUBLICATIONS

Pishnamazzade, B. F. et al., Zh. Org. Khim., 10 (4), 717-722 (1974).
Inukai, T. et al., Bulletin of the Chemical Society of Japan, vol. 45 891-894 (1972).
Inukai, T. et al., J. Org. Chem., 32, 869-871 (1967).
Inukai, T. et al., J. Org. Chem., 31, 1121-1123 (1966).
Inukai, T. et al., J. Org. Chem., 32, 872-875 (1967).
Inukai, T. et al., J. Org. Chem., 36, 924-928 (1971).
Textbook of Organic Chemistry, C. R. Noller, 547 (1951).
Kerimov, A. K. et al., Azerb. Khim. Zh., 3, 52-57 (1983).
Pishnamazzade, B. F. et al., Zh. Org. Khim., 10, (4), 712-717 (1974).
Pishnamazzade, B. F. et al., Zh. Org. Khim., 9, (4), 715-719 (1973).
Martirosyan, F. A. et al., Arm. Khim. Zh., 24 (8), 697-702 (1971).
Danishefsky, S. et al., J. Org. Chem., vol. 42, No. 10, 1819-1821 (1977).
Kojima, T. et al., J. Org. Chem., 35, 1342-1348 (1970).
Basic Principles of Organic Chemistry, J. D. Roberts et al., 262-265 (1964).
Jacobine, ACS Symp. Series, 417 (Radiation Curing of Polymeric Materials), pp. 160-175 (1990).
Martin, Chemical Reviews, vol. 61, pp. 537-562 (1961).

*Primary Examiner*—Joseph E. Evans
*Attorney, Agent, or Firm*—S. H. Hegedus

[57] ABSTRACT

Unsaturated cycloaliphatic esters like higher hydrocarbyl, functionally substituted or polyunsaturated cyclohex-3-ene carboxylates, made directly by cycloaddition of dienes with dienophillic (meth/eth)acrylates, and their derivatives like epoxides and urethanes, provide useful thermal and radiation curable coatings, inks, sealants, adhesives, solvents, acid scavengers, and intermediates for other uses.

5 Claims, No Drawings

PRODUCTION OF UNSATURATED CYCLOALIPHATIC ESTERS AND DERIVATIVES THEREOF

This application is a division of prior U.S. application Ser. No. 07/921,311, filing date Jul. 28, 1992 and which is a division of application Ser. No. 07/721,799 filing date Jun. 26, 1991, now abandoned.

BRIEF SUMMARY OF THE INVENTION

1. Technical Field

This invention relates to unsaturated cycloaliphatic esters produced by cycloaddition reactions and derivatives thereof, and more particularly to higher hydrocarbyl, functionally substituted or polyunsaturated cyclohex-3-ene carboxylates made by reacting dienes and dienophilic (meth/eth)acrylates, and especially 3,4-epoxy derivatives thereof useful in curable coatings.

2. Background of the Invention

Cycloaddition reactions of dienes, i.e., compounds having conjugated carbon-carbon double bonds, such as butadiene and cyclopentadiene, with dienophiles, i.e., α,β-unsaturated carbonyl compounds, such as acrylic acid, produce unsaturated cycloaliphatic carbonyl compounds. This reaction, also called the Diels-Alder reaction, is shown in Equation I.

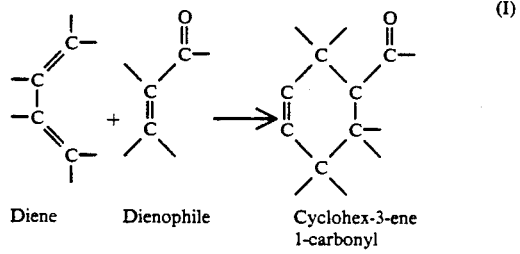

Diene    Dienophile    Cyclohex-3-ene 1-carbonyl (I)

Such reactions are well known and described in the literature. For example, U.S. Pat. No. 1,944,732 (Diels et al.) discloses reacting dienes with acrolein, acrylic acid and ethylidene ketone compounds. Dienophilic esters, such as ethyl acrylate, are disclosed by Roberts et al., in *Basic Principles of Organic Chemistry*, Pages 262–265, W. A. Benjamin, Inc., New York (1964). Additional studies of reactions between dienes and dienophiles are disclosed by Kojima et al., in "Aluminum Chloride Catalyzed Diene Condensation. V. Selectivity Reactivity Relationship of Dieneophiles toward Butadiene, Isoprene and 2-Trifluoromethylbutadiene", *Journal of Organic Chemistry*, 35, Pages 1342–1348 (1970). Reactions of 1-phenylseleno-2-trimethylsilyloxy-4-methoxy-1,3-butadiene and dienophiles are disclosed by Danishefsky et al., in "A Diels-Alder Route to Functionalized Cyclohexadienones", *Journal of Organic Chemistry*, Volume 42, Pages 1819–1821 (1977). Reaction of 2-chloro-3-phenyl-1,3-butadiene with the dienophiles of (meth)acrylic and cinnamic acids, or their methyl, ethyl and butyl esters, are disclosed by Martirosyan et al., in *Arm, Khim, Zh.*, 24(8), Page 697 (1971), *Chemical Abstracts*, 76:3514a.

Other cycloaddition reactions and derivitizations of cycloaliphatic compounds are also described in the literature. U.S. Pat. No. 2,794,812 (Philips et al.) discloses reacting dienes with dienophiles which are α,β-unsaturated aliphatic acids followed by esterification with alcohols and oxidation to produce 7-oxabicycloheptane 3-carboxylic acids and esters. U.S. Pat. No. 2,716,123 (Frostick et al.) discloses cyclic unsaturated aldehydes, made by reacting diene with α, β-unsaturated aliphatic aldehydes. These cyclic aldehydes are coupled by the Tischenko reaction between aldehydes to form the unsaturated dicycloalipbatic esters, which are epoxidized to make diepoxycycloaliphatic esters. U.S. Pat. No. 2,745,847 (Phillips et al.) discloses oxidizing unsaturated cycloaliphatic aldehydes to the corresponding unsaturated cycloaliphatic carboxylic acid, which are then reacted with glycols of aliphatic or oxyalkylene groups, i.e., dihydric alcohols to form unsaturated dicycloaliphatic esters which are then epoxidized to the corresponding diepoxides. Similarly, U.S. Pat. No. 2,750,395 (Phillips et al.) discloses reducing unsaturated cycloaliphatic aldehydes to the corresponding unsaturated cycloaliphatic alcohols, which are reacted with dicarboxylic acids to form unsaturated dicycloaliphatic esters which art epoxidized to the corresponding diepoxides. Various cyclohexene carboxylic esters, made by reacting cyclohezene carboxylic acid with various alkyl, phenyl and pbenylene ester chlorides are disclosed by Pishnamazzade et al., in *Zh. Org. Khim.*, 9(4), Pages 715–719 (1973), *Chemical Abstracts*, 79:31748k. These compounds are then epoxidized to form the corresponding epoxide. Bis(cyclohexene carboxylates), made by reacting cyclohexene carboxylic acid with ester dichlorides, and then oxidizing or halogenating to epoxy or dihalo products, are disclosed by Pishnamazade et al., in *Zh. Org. Khim*, 10(4), Pages 712–717 (1974), *Chemical Abstracts*, 81:25473s; and Kerimov et al., in *Azerb, Khim, Zh.*, (3), Pages 52–57 (1983), *Chemical Abstracts*, 100:191410z.

Production of various, such as functionally substituted or multifunctional, unsaturated cycloaliphatic compounds has involved multiple reactions. For example, diene is reacted with dienophilic acid or aldehyde to produce unsaturated cycloaliphatic acid or aldehyde. The aldehyde is then reduced to the corresponding alcohols, oxidized to the corresponding acid, or co-reacted to produce corresponding di(esters). Through further reactions, the unsaturated cycloaliphatic acids are esterified either directly with alcohols or using base to form the corresponding salt and reaction with halides for further derivatization. These procedures require multiple reactions and/or produce by-products, such as salts, requiring disposal. Of course, a by-product, KCl, which had to be removed and properly disposed of in additional steps, was formed with the earlier-cited reaction sequence of Kerimov et al. It would be desirable if a more direct procedure could be provided for producing certain unsaturated cycloaliphatic esters.

SUMMARY OF THE INVENTION

This invention relates to a process for producing unsaturated cycloaliphatic esters represented by Formula 1.

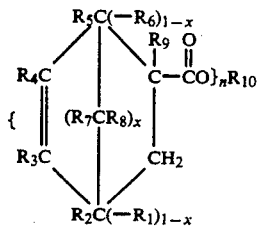

(1)

In Formula 1: n is at least 1; $R_{1\text{-}8}$ independently, hydrogen, $C_{1\text{-}10}$ hydrocarbyl with or without halo substitution, halo, cyano, or silyl; $R_9$ is hydrogen, methyl, or ethyl; $R_{10}$ is hydrocarbyl or oxyhydrocarbyl, provided $R_{10}$ has at least 5 carbon atoms or is oxyhydrocarbyl or is —CH=CH$_2$ when n is 1; and x is 0 or 1. The process comprises a reaction using diene represented by Formula 2.

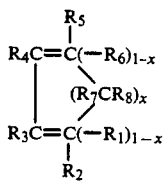

(2)

In Formula 2, $R_{1\text{-}8}$ and x are as defined in Formula 1. The diene is reacted with a dienophilic (meth/eth)acrylate represented by Formula 3.

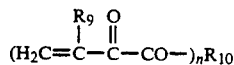

(3)

In Formula 3, n and $R_{9\text{-}10}$ are as defined in Formula 1.

This invention also relates to processes for epoxidizing, hydrogenating and transesterifying unsaturated cycloaliphatic esters represented by Formula 1 above. The unsaturated cycloaliphatic esters can be prepared by reacting a compound with a system of conjugated carbon-carbon multiple bonds with an acrylate through a Diels-Alder reaction as indicated above. Then, in subsequent reactions, these unsaturated cycloaliphatic esters can be either oxidized with an oxidizing agent such as peracetic acid to a cycloaliphatic epoxide or reduced to the saturated compound by means of hydrogenation. The compounds of the invention can also be produced by transesterifying the unsaturated or saturated compound or the epoxidized compound with other suitable compounds. The compounds of this invention can be made by a variety of processes that include Diels-Alder reactions followed by subsequent epoxidation or hydrogenation, Diels-Alder reactions followed by epoxidation or hydrogenation and subsequent transesterification or transetherification, Diels-Alder reactions followed by transesterification or transetherification and subsequent epoxidation or hydrogenation and the like.

This invention further relates to unsaturated cycloaliphatic esters of Formula 1 above and derivatives therof including derivatives formed by epoxidation, hydrogenation, transesterification and the like.

DETAILED DESCRIPTION

It has been found that unsaturated cycloaliphatic esters having higher hydrocarbyl or functionally substituted alcohol moiety or polyunsaturation can be made from diene with dienophilic (meth/eth)acrylate ester. The esters are produced without the need for multiple reaction steps or unnecessary by-product. Thus, in a single reaction step, a compound is made, without any by-product formation, that previously required up to three reaction steps for its manufacture, i.e., first formation of the cyclohex-3-ene carboxylate, then reaction of the carboxylate with a base to form the potassium salt, and finally reaction of the potassium salt with an alkyl or other chloride (see Kerimov et al., noted previuosly).

The term "hydrocarbyl" is used in this specification to mean any radical containing hydrogen and carbon atoms. The term "oxyhydrocarbyl" is used in this specification to mean any radical containing oxygen, hydrogen and carbon atoms.

Cycloaddition

Dienes which may be used include those shown in Formula 2 wherein $R_{1\text{-}8}$ and A are as defined in Formula 1. When x is 0, the diene is an acyclic, conjugated diene, represented by Formula 4.

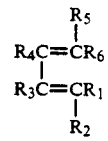

(4)

In Formula 4, $R_{1\text{-}6}$ are as defined in Formula 1. When x is 1, the diene is a cyclopentadiene, represented by Formula 5.

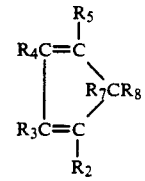

(5)

In Formula 5, $R_{2\text{-}5}$ and $R_{7\text{-}8}$ are as defined in Formula 1. In Formulas 2, 4 and 5, four or more of $R_{1\text{-}8}$ are preferably hydrogen, more preferably $R_3$ or $R_4$ are hydrogen, and most preferably $R_3$ and $R_4$ are both hydrogen.

Illustrative diene substituents, represented by $R_{1\text{-}8}$ in Formulas 2, 4 and 5, include, among others: hydrogen; alkyl such as methyl, ethyl, propyl, butyl, etc.; aryl such as phenyl; cycloalkyl such as cyclohexyl; halo-substituted hydrocarbyl such as polyfluoromethyl; halo such as fluoro, chloro, bromo, iodo, etc.; cyano; and silyl such as polymethylsilane.

Suitable dienes include, among others, one or more: 1,3-butadiene; homologs of butadiene; isoprene; homologs of isoprene; 1,3-pentadiene; cyclopentadiene; myrcene; phellandrene; 1,3-hexadiene; 2,4-hexadiene; 1,3,5-hexatriene; 1,3-octadiene; 2,4-octadiene; 3,5-octadiene; 1,3,5,7-octatetraene; 2-trifluoromethyl-1,3-butadiene; 1-methyl-1,3-butadiene; 2-methyl-1,3-butadiene; 1-phenyl-1,3-butadiene; 2-phenyl-1,3-butadiene; 1-cyclohexyl-1,3-butadiene; 2-cyclohexyl-1,3-butadiene; 1-cyclohexyl-1,3-isoprene; 2-cyclohexyl-1,3-isoprene; 1-chloro-1,3-butadiene; 2-chloro-1,3-butadiene; 1-cyano-1,3-butadiene; 2-cyano-1,3-butadiene; 2,3-dimethyl-1,3-butadiene; and the like. Preferred dienes include 1,3-butadiene, isoprene and cyclopentadiene.

Dienophilic (meth/eth)acrylates, i.e. dienophiles, are as shown in Formula 3. In Formula 3, $R_{9-10}$ and n are as defined in Formula 1. The number of acrylic groups, defined by p, is typically from 1 to about 10, and when polyacrylic is preferably from 2 to about 6. $R_9$ is preferably hydrogen or methyl, and most preferably hydrogen.

Illustrative $R_{10}$ groups include, among others: $C_{5+}$ alkyl such as pentyl, hexyl, octyl dodecyl, hexadecyl, and so on; aryl such as phenyl; cycloalkyl such as cyclohexyl; vinyl; alkoxy such as ethoxy; aryloxy such as phenoxy; hydroxyalkyl such as hydroxy ethyl, hydroxypropyl, 2-ethyl-2-hydroxyethyl, and so on; alkoxylated hydroxyalkyls, including addition products of hydroxyalkyls with alkylene oxides like ethylene oxide, propylene oxide, tetrahydrofurans, methoxytetrahydrofurans, lactones like caprolactone and valerolactone and propiolactone, such as $-CH_2CH_2-O-(CH_2CH_2O)_m-H$, $-CH_2CHCH_3-O-(CH_2CH_2O)_m-H$, $-CH_2CH_2-O-(CH_2CHCH_3O)_m-H$, $-CH_2CHCH_3-O-(CH_2CHCH_3O)_m-H$, $-CH_2CH_2-O-((CH_2)_4O)_m-H$, $-CH_2CHCH_3-O-((CH_2)_4)_m-H$, $-CH_2CH_2-O-((CH_2)_5O)_m-H$, $-CH_2CHCH_3-O-((CH_2)_5)_m-H$, $-CH_2CH_2-O-(CO(CH_2)_5O)_m-H$, $-CH_2CHCH_3-O-(CO(CH_2)_5O)_m-H$, and the like where M is from 1 to about 25, preferably from 1 to about 10; or the residue formed by reacting (meth/eth)acrylic acid with polyhydroxy compound, i.e., compounds having 2 or more hydroxyl groups, providing polyvalent residue $R_{10}$. For example, $R_{10}$ is $CH_3CH_2C(CH_2O-)_3$ with n equal to 3 or is $-O-CH_2CH_2-O-CH_2CH_2-O-$ with n equal to 2 when the polyhydroxy compound is trimethylolpropane or diethylene glycol, respectively. Illustrative polyhydroxy compounds include, among others, one or more: ethylene glycol; diethylene glycol; triethylene glycol; tetraethylene glycol; trimethylolpropane; pentaerythritol; 1,3-butylene glycol; polyethylene glycol; caprolactone; tripropylene glycol; poly(rpopylene glycol); Bisphenol A; linseed oil; soybean oil; as well as alkoxylated derivatives of such polyhydroxy compounds.

Illustrative dienophilic (meth/eth)acrylates, by which is meant acrylates, methacrylates, and ethacrylates, include, among others, one or more: esters of (meth/eth)acrylic acid with monohydric and polyhydric compounds, such as pentyls, hexyls, octyls, decyls, and the like; neopentyl diacrylate; esterdiol diacrylates such as 2,2-dimethyl-3-hydroxypropyl-2,2-dimethyl-3-hydroxypropionate diacrylate; trimethylolpropane triacrylate; pentaerythritol di-, tri-, and tetraacrylate; hydroxyethyl acrylate; hydroxypropyl acrylate; (poly)-caprolactone acrylates; ethoxylated acrylates; propyoxylated acrylates; glycerol acrylates; triethylene glycol diacrylate; tetraethylene glycol diacrylate; ethoxyethyl acrylate; cyclohexyl acrylate; 2-phenoxyethyl acrylate; isobornyl acrylate; 1,3-butylene glycol diacrylate; 1,4-butanediol diacrylate; 1,6-hexanediol diacrylate, glycidyl acrylate; dipentaerythritol acrylates; poly(ethylene glycol) acrylates; caprolactone di-, tri-, and tetracrylates, as well as other lactone acrylates; tripropylene glycol diecrylate; poly(propylene glycol) acrylates; ethoxylated or propoxylated Bisphenol-A diacrylates; alkoxylated esterdiol diacrylates such as ethoxylated or propoxylated 2,2-dimethyl-3-hydroxypropyl-2,2-dimethyl-3-hydroxypropionate diacrylates; acrylates of caprolactone reacted with esterdiols; ethoxylated or propoxylated trimethylolpropane triacrylate; ethoxylated or propoxylated pentaerythrtiol di-, tri-, or tetraacrylate; unsaturated polyesters containing ethylenic unsaturation from maleic, fumaric, citraconic acids and the like; unsaturated dicarboxylic acids; urethane acrylates of various types; epoxy acrylates; acrylated polybutadiene; acrylated linseed oil; acrylated soybean oil; and the like. In one embodiment, mixtures of multifunctional and monofunctional dienophiles can be used with monofuntional dienophile having $R_{10}$ hydrocarbyl groups with 1 or more carbon atoms.

The diene reacts with the dienophilic (meth/eth)acrylate, which undergoes 1,4-cycloaddition, to produce cyclohex-3-ene-1-carboxylates. Of course, as is understood by those skilled in the art, a variety of isomers can be obtained. Acyclic dienes, when x is 0, react with monofunctional, when n is 1, or polyfunctional, when n is more than 1, (meth/eth)acrylates as shown in Equation II and III, respectively.

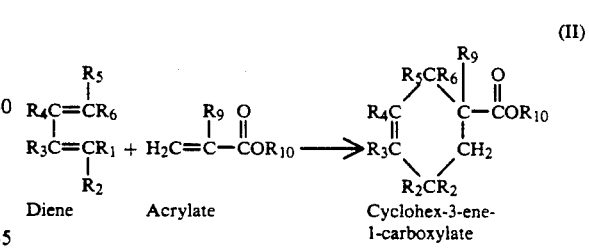

(II)

Diene    Acrylate    Cyclohex-3-ene-1-carboxylate

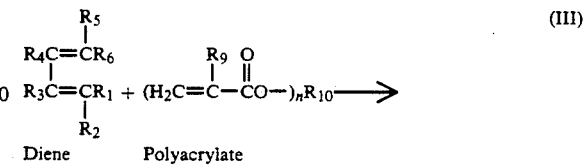

(III)

Diene    Polyacrylate

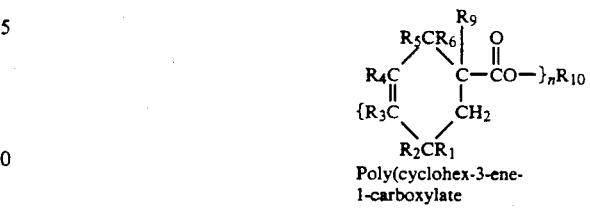

Poly(cyclohex-3-ene-1-carboxylate)

Cyclic dienes, when x is 1, react with monofunctional or polyfunctional (meth/eth) acrylates as shown in Equations IV and V, respectively.

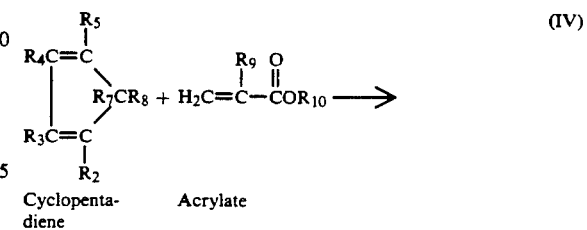

(IV)

Cyclopentadiene    Acrylate

-continued

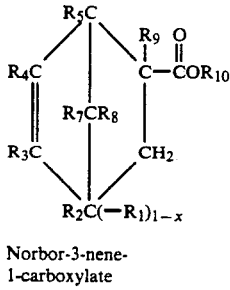

Norbor-3-nene-
1-carboxylate

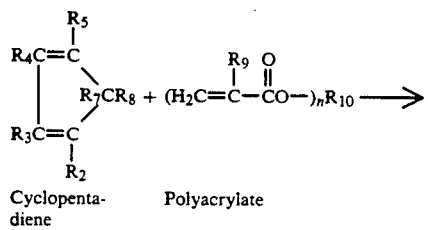

Cyclopenta-    Polyacrylate
diene

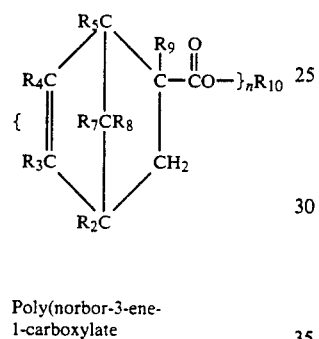

Poly(norbor-3-ene-
1-carboxylate)

The relative proportion of diene to dienophile is not narrowly critical and may vary depending on the degree of functionality, i.e. number of acrylic groups, in the dienophilic (meth/eth)acrylate. Usually, the amount of diene to dienophile (meth/eth)acrylate is from about 5:1 to about 0.1:1, preferably from about 3:1 to about 0.2:1 and most preferably from about 2:1 to about 0.5:1, moles of diene per mole of ethylenic unsaturation in the dienophilic (meth/eth)acrylates.

The particular reaction conditions for cycloaddition are not critical but can be any effective, including known, procedures for reacting dienes with dienophiles sufficient to produce the unsaturated cycloaliphatic esters. The reaction is usually carried out at temperature from about $-100°$ C. to about $80°$ C., preferably $-10°$ C. to about $50°$ C. The reaction may be conducted under atmospheric, i.e. ambient, subatmospheric or superatmospheric pressures, preferably at subatmospheric or atmospheric pressures, and most preferably at subatmospheric pressures.

Other ingredients may optionally be provided to the cycloaddition reaction. Catalyst may be used to improve reaction rate and the ratio of isomers produced, such as described by Sauer et al. in *Tetrahedron Letters*, (7), Pages 731–736 (1966). Suitable catalysts include, among others, one or more: aluminum chloride, aluminum (tri)chloride (di)etherate, boron trifluoride etherate, tin (IV)chloride, titanium tetrachloride, and others, and particularly methyl acrylate-aluminum chloride complex as described by Kojima et al. in the *Journal of Organic Chemistry*, 35(5), Page 1342 (1970). Suitable solvents may optionally be used, including, among others, one or more: methylene chloride, dioxane, methanol, ethanol, propanol, isopropanol, chloroform, dioxane, triethylamine, 1,2-dimethoxyethane, acetone, toluene, and others. Special solvents, such as lithium perchlorate in diethyl ether as described by Gaul in the *Journal of the American Chemical Society*, 112, Page 4595 (1990) may be used to accelerate the reaction.

The unsaturated cycloaliphatic esters so produced have mono- or polyunsaturation, as defined by m equal to 1 or greater than 1, respectively. When monofunctional, the esters have an alcohol moiety, of $R_{10}$, which is either hydrocarbyl having at least 5 carbon atoms or oxyhydrocarbyl, including functional groups like hydroxyl.

Transesterification

A particularly useful technique for preparing a variety of unsaturated cycloaliphatic carboxylates and particularly multifunctional unsaturated cycloaliphatic carboxylates, is transesterification. Unsaturated cycloaliphatic esters can undergo transesterification by reaction with hydroxyl-containing compound, as set forth in Equation VI.

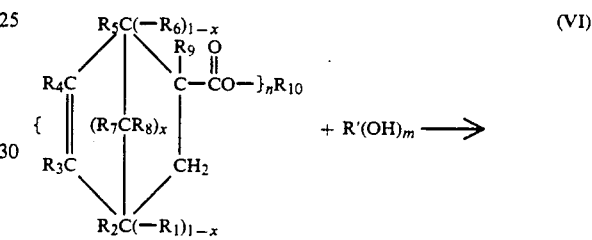

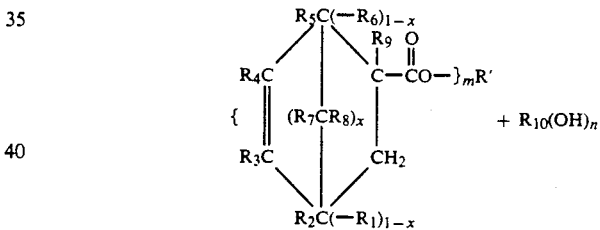

In Equation VI, n, $R_{1-10}$ and x are as defined in Formula 1; m identifying the number of hydroxyl groups in hydroxyl-containing compound $R'(OH)_m$, is at least one, preferaby from 1 to about 10; and $R'$ is the residue of the hydroxyl-containing compound. Suitable hydroxyl-containing compounds include, among others, one or more: alcohols, such as methanol, ethanol, propanols, butanols, pentanols, hexanols, cyclohexanols, phenols, decanols, dodecanaols, hexadecanols and others; glycols, such as ethylene glycol di-, tri-, tetraethylene glycols and other poly(ethylene glycols), propylene glycol, di-, tri-, and tetrapropylene glycol as well as other poly(propylene glycols); polyols such as trifunctional poly(propylene oxide)s including ethylene oxide-capped and $\epsilon$-caprolactone-capped propylene oxide polyols that contain up to about 25% by weight ethylene oxide or $\epsilon$-caprolactone oxide, random, block, and graft ethylene oxide/propylene oxide copolymers, polylactone polyols including $\epsilon$-caprolactone, various methyl caprolactone, $\epsilon$-valerolactone and methyl valerolactone, propiolactone polyols, poly(teramethylene oxide) polyols, polyester polyols including hexanediol adipates, butylene adipates, ethylene adipates, butylene succinates, polycarbonate polyols, hydroxyl-terminated polyethylenes, poly(vinyl alcohol), vinyl acetate/vinyl alcohol copolymers, styrene/allyl alcohol copolymers, hydroxyethyl cellulose, hydroxypropyl cellulose, cellulose acetates, hydroxylalkyl acrylates like hydroxyethyl acrylate and hydroxypropyl acrylate alone or after reaction with various amounts of propylene oxide or ethylene oxide, lactones like caprolactone acrylates that contain one or more free hydroxyl groups, and others.

The particular reaction conditions for transesterification are not critical but can be any effective, including known, procedures for reacting esters with hydroxy compounds sufficient to produce the unsaturated cycloaliphatic transesters. The reaction temperature may vary depending on the particular reactants used and is usually carried out at temperature from about 40° C. to about 30° C., preferably 60° C. to about 250° C. The reaction may be conducted under atmospheric, i.e. ambient, subatmospheric or superatmospheric pressures, preferably at subatmospheric or atmospheric pressures.

Other ingredients may optionally be provided to the transesterification reaction. Catalyst may be used. Suitable transesterification catalysts include, among others, one or more: tetrabutyltitanate; zinc acetate; titanium dioxide; sodium and potassium alkoxides; sodium and potassium phenoxides; lead oxide; ion exchange resins; and others. Time for conducting the transesterification reaction can vary generally from about 10 minutes to 40 or more hours, depending on the temperature employed and particular ingredients involved. Specific reaction conditions for transesterification may be determined based on known techniques, such as described by Tucek et al. in *Acta Polymerica*, 31(7), page 429 (1980).

Epoxidation

The unsaturated cycloaliphatic esters can be epoxidized to form cycloaliphatic epoxides and other, useful products, as shown in Equation VII.

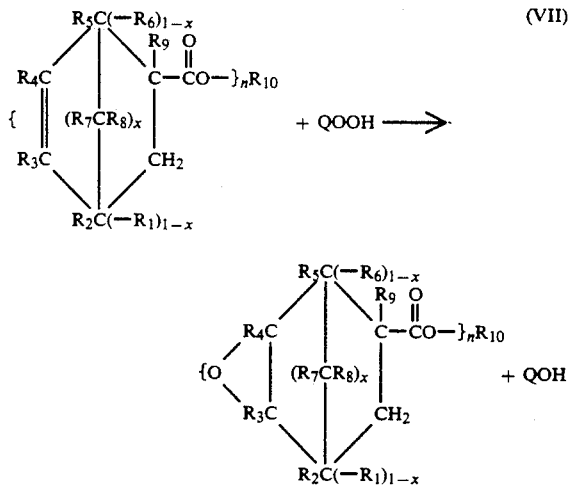

In Equation VII, n, $R_{1-10}$ and x are as described in Formula 1, QOOH is an epoxidizing agent and QOH is the residue of the epoxidizing agent after epoxidation.

The unsaturated cycloaliphatic compounds can be epoxidized by any suitable, including known, means to form monofunctional or polyfunctional cycloaliphatic epoxides. Suitable epoxation procedures are disclosed in U.S. Pat. Nos. 2,716,123, 2,745,847, and 2,750,395; by Lee et al. in the *Handbook of Epoxy Resins*, McGraw-Hill Book Co., New York (1967), and by May et al. in *Epoxy Resins Chemistry and Technology*, Marcel Dekker, Inc., New York (1973).

Any suitable, including known, epoxidizing agents, shown as QOOH is Equation VII, can be used. Usually, these agents can be formed in situ from hydrogen peroxide and an organic acid such as acetic acid, can be preformed and used as a peracid, or can be in the form of a dioxirane such as dimethyldioxirane. Illustrative peracids include, among others: perbenzoic acid; peracetic acid; perpropionic acid; perbutyric acid; percaproic acid; m-chloro-peroxybenzoic acid; perlactic acid; permonochloroacetic acid; permonosuccinic acid; t-butyl-perbenzoic acid; and others. The peracids are usually dissolved in a solvent, such as ethyl acetate, to minimize explosive and other hazards.

The epoxidation reaction conditions are not critical and may be any suitable, including known, conditions for achieving epoxidation. Suitable temperatures range from less than about 5° C. to about 90° C., preferably from about 25° C., to about 60° C. The time required for reaction can vary depending upon the particular reactants charged, the temperature, and the batch size of the reaction mixture, such as well known to those skilled in the art of epoxidation chemistry. Usually, the oxidizing agent solution is carefully and very slowly added to the reactor containing the unsaturated compound, in either a neat form or dissolved in a suitable solvent, such as ethyl acetate, and held at a constant reaction temperature. The rate of oxidizing agent addition should be such that a desired maximum temperature is not exceeded. The exothermic oxidation reaction is controlled by cooling the reactants to the desired reaction temperature. Oxidizing agent addition is decreased or stopped when necessary to maintain temperature control. The reacting mixture may be quenched, such as by using an ice/water bath. The reaction product can be isolated by vacuum stripping of the oxizidiating agent by-product, such as acetic acid, that is formed and the solvent that had been used to dissolve the unsaturated cyclicaliphatic ester and/or oxidizing agent. If desired, the product may be redissolved and reisolated by vacuum stripping using conventional techniques. Other oxidation procedures, such as those employing acetaldehyde monoperacetate, hydrogen peroxide and in situ peracid generation, and the like, can also be used.

Other Derivatizations

Unsaturated cycloaliphatic esters can be reacted with hydrogen, as illustrated in Equation VIII, to form saturated cycloaliphatic esters, useful as solvents or as intermediates to other end uses.

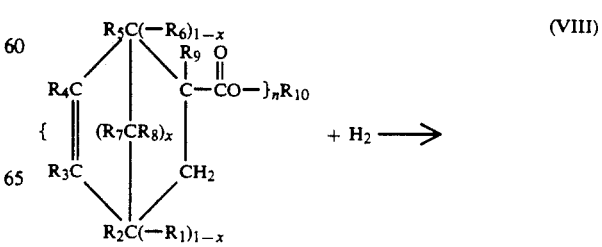

-continued

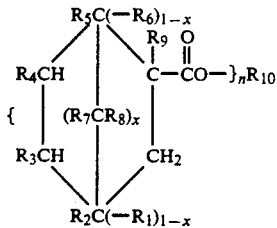

The particular reaction conditions for hydrogenation are not critical but can be any effective, including known, hydrogenation procedures sufficient to produce the saturated cycloaliphatic esters. The reaction may be carried out at generally temperature from about 10° C. to about 250° C., preferably from about 20° C. to about 200° C. The reaction may be conducted at pressures of about 0 to about 500 psig, and preferably from about 0 to about 200 psig.

Other ingredients may optionally be provided to the hydrogenation reaction. Suitable hydrogenation catalyst may be used including, among others: platinum; nickel; palladium; iron; cobalt molybdate on alumina; copper chromite; barium promoted copper chromite; tin-copper couple; zinc-copper couple; Raney-type compounds, such as Raney-nickel, aluminum-cobalt, aluminum-copper, and aluminum-nickel; and others.

Various unsaturated cycloaliphatic esters, such as those with hydroxyl groups, can be condensed with various mono- and polyfunctional carboxylic acids or anhydrides or their mixtures as set forth in Equation IX.

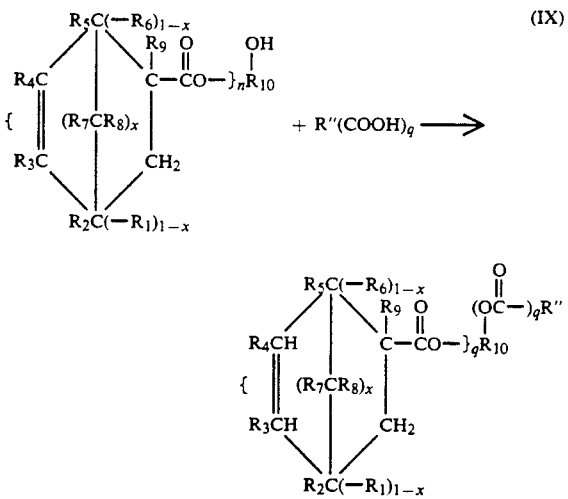

In Equation IX: n, $R_{1\text{-}10}$ and are as defined in Formula I including wherein $R_{10}$ also has a hydroxyl group; R" is hydrocarbyl; and g is at least 1. $R''(COOH)_g$ is a monofunctional, when g is 1, or a polyfunctional, when g is more than 1, carboxylic acid, or may be the corresponding anhydride. Unsaturated cycloaliphatic esters having one or more free hydroxyl groups can be reacted with compounds like lactones such as ε-caprolactone, methyl caprolactones, ε-valerolectone, methyl valerolactones, ζ-enantholactones, β-proprio-lactones, and others, or with propylene oxide, ethylene oxide, tetrahydrofuran, or mixtures of these compounds to form new adducts, which can react with the carboxylic acids and/or anhydrides, with or without subsequent epoxidation.

Other derivatization reactions involving the unsaturated cycloaliphatic esters include transetherification reactions. The particular reaction conditions for transetherification are not critical and include conventional procedures known in the art.

It is understood that the various derivatization reactions can be conducted in any permissible sequence. This invention is not to be construed as being limited to particular derivatization reactions or derivatization reaction sequences following the Diels-Alder reaction.

Uses

The unsaturated cycloaliphatic esters, and derivatives thereof, especially epoxides, can be used alone or in combination with a variety of other ingredients such as hydroxyl-containing compounds, other cycloaliphatic epoxides and glycidyl epoxides, acrylates, and other suitable ingredients to form coatings, inks, adhesives, sealants, in the photoresist market area for production of printing plates, printed circuit boards, and similar products. The ingredients may be reacted together by actinic radiation, such as ultraviolet light, with suitable photoinitiators, under suitable, such as ambient, conditions, or by means of thermal energy, when suitable blocked or free initiators or catalysts are employed.

The cycloaliphatic epoxides of this invention are useful alone or in combination with other compounds to form a variety of articles of commerce including molded parts; coatings, inks, adhesives, and sealants cured by both thermal and ultraviolet light means as indicated above; acid scavengers; pharmaceutical products or intermediates for pharmaceutical products; flavors and fragrances; solvents; as well as other end uses. The epoxidized compounds of this invention may be used alone or in combination with other ingredients such as polyether, polyester, polycarbonate, and polylactone polyols; linear and cyclic vinyl ethers; anhydrides, and other ingredients known to those skilled in the art of product formulation. The unsaturated cycloaliphatic reaction products that are reduced or hydrogenated according to this invention have utility as solvents for various purposes such as dissolving polymers, decreasing viscosity of paint systems, paint removal, and the like.

Hydroxyl-containing compounds that can be used in combination with the epoxidized cycloaliphatic esters or other derivatives include, among others: alcohols such as butanols, pentanols, hexanols, decanols, ethoxy and propoxy alcohols such as ethoxyethanol, propoxyethanol, ethoxypropanol, propoxypropanol, ethoxybutanol, propoxybutanol, ethoxyethoxy- and propoxypropoxy-ethanol, propanol, or butanol; glycols such as ethylene glycol, di-, tri-, tetra-ethylene glycols and other poly(ethylene glycols), propylene glycol, di-, tri-, and tetrapropylene glycol as well as other poly(propylene glycols); polyols such as trifunctional poly(propylene oxide) polyols including ethylene oxide-capped and ε-caprolactone-capped propylene oxide polyols that contain up to above 25% ethylene oxide, or caprolactone as the capping compound, random, block, and graft ethylene oxide/propylene oxide copolymers, polylactone polyols including ε-caprolactone, various methyl caprolactone, ζ-valerolactone and methyl valerolactone, propiolactone polyols, poly(tetramethylene oxide) polyols, polyester polyols including hexanediol adipates, butylene adipates, ethylene adipates, butylene succinates, polycarbonate polyols, hydroxyl-terminated polyethylenes, styrene/allyl alcohol copolymers, hydroxyethyl cellulose, hydroxypropyl cellulose; and others. In the radiation and thermal cure formulations, these compounds serve to increase reaction rate and, when molecular weight is sufficiently high, to toughen and/or flexiblize the formed product.

Suitable epoxides that can be used in combination with the epoxidized cycloaliphatic esters and if desired other ingredients including cycloaliphatic epoxides having an average of one or more epoxide groups per molecule, including, among others: 3,4-epoxycyclohexylmethyl 3,4-epoxycyclohexane carboxylates such as 3,4-epoxy-cyclohexylmethyl 3,4-epoxycyclohexane carboxylate, 3,4-epoxy-1-methylcyclohexylmethyl 3,4-epoxy-1-methylcyclohexane carboxylate, 6-methyl 3,4-epoxycyclohexylmethyl 6-methyl-3,4- epoxycyclohexane carboxylate, 3,4-epoxy-3-methyl-cyclohexylmethyl 3,4-epoxy-3-methylcyclohexane carboxylate; 3,4-epoxy-5-methylcyclohexylmethyl 3,4-epoxy-5-methylcyclohexane carboxylate, and as described in, for example, U.S. Pat. No. 2,890,194; diepoxides of cycloaliphatic esters of dicarboxylic acids such as bis(3,4-epoxycyclohexylmethyl)oxylate, bis(3,4-epoxycyclohexylmethyl)adipate, bis(3,4-epoxy-6-methylcyclohexylmethyl)adipate, bis(3,4-epoxycyclohexylmethyl)pimelate, and as described in, for example, U.S. Pat. No. 2,750,395; other cycloaliphatic diepoxides including 2-(3,4-epoxycyclohexyl-5,5-spiro-3,4-epoxy)cyclohexane-m-dioxane, halogen or monovalent hydrocarbon variations of this compound, and the like as further defined in U.S. Pat. No. 3,318,822; cyclopentadiene diepoxide, cyclohexane diepoxide; and preferably 3,4-epoxycyclohexylmethyl-3,4-epoxycyclohexane carboxylate, bis(3,4-epoxycyclohexylmethyl)adipate, 2-(3,4-epoxycyclohexyl-5,5-spiro-3,4-epoxy)cyclohexane-m-dioxane, or mixtures thereof.

Cycloaliphatic monoepoxides may also be used, in combination with the epoxidized cycloaliphatic esters, which may be an unsubstituted monoepoxide, such as cyclohexene oxide, or a monoepoxide substituted with, for example, alkyl groups of 1 to 6 carbon atoms, halogen, ester groups, vinyl groups, and others. Suitable substituted monoepoxides include, among others: limonene monoepoxide; 4-vinyl cyclohexene monoepoxide; norbornene monoepoxide; alpha-pinene monoepoxide; and preferably vinyl substituted or alkyl substituted monoepoxide like 4-vinyl-1,2-epoxycyclohexane, 4-vinyl-1,2-epoxynorbornene, or limonene monoepoxide. The amount of cycloaliphatic mono- or diepoxide present in any suitable, including known, from 0 to about 40, preferably from about 1 to about 30, and most preferably from about 1 to about 20 weight percent based on the amount of the epoxidized cycloaliphatic ester.

If desired, minor amounts of glycidyl epoxides such as the diglycidyl ethers of Bisphenol-A, diglycidyl ethers of brominated Bisphenol-A, cresol-novolac epoxy resins, epoxy phenol novolac resins, diglycidyl ethers of 1,4-butanediol, and the like can be combined with the epoxidized cycloaliphatic esters.

Radiation-curable compositions may contain substituted and unsubstituted, linear or cyclic, vinyl ethers, such as acrolein dimer, acrolein tetramer, 2-methoxy tetrahydropyran, pyran, 2-methoxy dihydropyran, triethylene glycol divinyl ether, 1,4-cyclohexanedimethanol divinyl ether, butyl vinyl ether, and others.

Photoinitiators which may be used in the photocurable compositions include, among others, one or more: metal fluoroborate; complex of boron trifluoride, as described in U.S. Pat. No. 3,379,653; bis(perfluoroalkylsulfonyl)methane metal salt, as described in U.S. Pat. No. 3,586,616; aryl diazonium compound as described in U.S. Pat. No. 3,708,296; aromatic onium salt of Group VIa elements as described in U.S. Pat. No. 4,058,400; aromatic onium salt of Group Va elements as described in U.S. Pat. No. 4,069,055; dicarbonyl chelate of a Group IIIa-Va element as described in U.S. Pat. No. 4,068,091; thiopyrylium salt as described in U.S. Pat. No. 4,139,655; Group VIb element in an $MF_6$-anion where M is selected from phosphorous, antimony, and arsenic as described in U.S. Pat. No. 4,161,478; arylsulfonium complex salt as described in U.S. Pat. No. 4,231,951; aromatic iodonium complex salt and aromatic sulfonium complex salt, as described in U.S. Pat. No. 4,256,828; bis(4-(diphenylsulfonio)-phenyl) sulfide-bis-hexafluorometallic salts such as the phosphate, arsenate, antimonate and the like as described Watt et al. in *J. Polymer Sci.*: Polymer Chem. Ed., 22, 1789 (1984); and preferably cationic photoinitiators including arylsulfonium complex salts, aromatic sulfonium or iodonium salts of halogen containing complex ions, and aromatic onium salts of Group II, V, and VI elements, such as FX-512 (3M Co.), UVR-6990 and UVR-6974 (Union Carbide Chemicals and Plastics Co. Inc.), UVE-1014 and UVE-1016 (General Electric Co.), KI-85 (Degussa), and SP-150 and SP-170 (Asahi Denka). The photocurable composition may also contain benzophenone or a derivative of benzophenone.

These photoinitiators generate both cations, which cause polymerization of the epoxidized cycloaliphatic esters, and free radicals, which can be used to polymerize acrylates, such that photocurable compositions may also contain acrylates. Suitable acrylates may be derived from ethylenically unsaturated monomers such as: esters of acrylic and methacrylic acid with monohydric and polyhydric compounds, such as methyl, ethyl, propyl, butyl, pentyl, hexyl, octyl, decyl, and the like acrylates and methacrylates; like neopentyl diacrylate, esterdiol diacrylates such as 2,2-dimethyl-3-hydroxypropyl-2,2-dimethyl-3-hydroxypropionate diacrylate, trimethylolpropane triacrylate, pentaerythriol di-, tri-, and tetraacrylate, hydroxyethyl acrylate, hydroxypropyl acrylate, caprolactone acrylates, ethoxylated acrylates, propyoxylated acrylates, glycerol acrylates, triethylene glycol diacrylate, tetraethylene glycol diacrylate, ethoxyethyl acrylate, cyclobexyl acrylate, 2-phenoxyethyl acrylate, isobornyl acrylate, 1,3-butylene glycol diacrylate, 1,4-butanediol diacrylate, 1,6-hexanediol diacrylate, glycidyl acrylate, or the corresponding methacrylates; styrene; divinylbenzene; N-vinylpyrrolidone; and others. Oligomers or polymers which can be used in photopolymerizable compositions include, among others: poly(ethylene glycol) acrylates; caprolactone di-, tri-, and tetracrylates; tripropylene glycol diacrylate; poly(propylene glycol) acrylates; ethoxylated or propoxylated Bisphenol A diacrylates; alkoxylated esterdiol diacrylates, such as ethoxylated or propoxylated 2,2-dimethyl-3-hydroxypropyl-2,2-dimethyl-3-hydroxypropionate diacrylates; acrylates of caprolactone reacted with esterdiols; ethoxylated or propoxylated trimethylolpropane triacrylate; ethoxylated or propoxylated pentaerythriol di-, tri, or tetracrylate; unsaturated polyesters containing ethylenic unsaturation from maleic, fumaric, citraconic, or other unsaturated dicarboxylic acids; urethane acrylates; epoxy acrylates; acrylated polybutadiene; acrylated linseed oil; acrylated soybean oil; and others. Photocurable compositions may also contain homolytic fragmentation-type, free radical-generating photoinitiator when acrylates are present.

Photopolymerization may be carried out by exposing the film or coating containing the unsaturated cycloaliphatic esters or derivatives to electromagnetic radiation which is rich in short-wave radiation. Particularly useful is radiation of about 200 to about 400 nanometers in wavelength. Illustrative of appropriate light sources are low pressure, medium pressure, and high pressure mercury vapor lamps, xenon and other flash-type lamps, fluorescent lights, lasers, electrodeless mercury lamps, and the like. Other sources of radiant energy such as electron beams, gamma radiation, X-rays, sunlight, and so on can also be used.

The photocurable compositions may contain, exclusive of photoinitiator, from about 25 to 100 percent of the cycloaliphatic epoxides, from 0 to about 60 percent of hydroxyl-containing compound, from 0 to about 75 percent of other cycloaliphatic or other epoxide, from 0 to about 60 percent vinyl ether, and from 0 to about 60 percent acrylate. The photocurable compositions may also contain other ingredients such as one or more surfactants, flow and leveling agents, fumed silicas, silicone oils and other slip agents, and other ingredients suitable for coatings.

The thermally-curable compositions can contain suitable, including known, catalysts such as sulfuric acid, hydrochloric acid, p-toluene sulfonic acid, methyl sulfonic acid, phosphoric acid and alkyl derivatives of phosphoric acid, maleic acid, trimellitic acid, triflic acid, salts of triflic acid such as the diethylammonium salt of triflic acid, the ammonium salt of triflic acid, the stannous salt of triflic acid, stannous octanoate, uranyl nitrate, zinc octanoate, and the like, including mixtures of these catalysts. The thermally-curable compositions may contain, exclusive of catalyst, from about 25 to 100 percent of the cycloaliphatic epoxides, from 0 to about 60 percent of a hydroxyl-containing compound, and from 0 to about 75 percent of other cycloaliphatic or other epoxide. The thermally-curable compositions may also contain other ingredients such as one or more surfactants, flow and leveling agents, fumed silicas, silicone oils and other slip agents, and other ingredients suitable for coatings.

The crosslinkable coating compositions can also contain other suitable ingredients like pigments, fillers, surfactants, flow and leveling agents, fumed silica, slip agents, and other additives useful in coating compositions, in suitable, including known, quantities. Selection of particular coating additives may follow established practice. In preparing the crosslinkable polymeric coating compositions, the ingredients can be mixed by any suitable means, including conventional procedures used in the production of paint, ink, adhesive, and sealant compositions. The coating compositions may be applied to a surface or substrate by any suitable, including conventional, means. Thermal curing can be conducted by heating at a suitable temperature generally from about 50° C. to about 275° C., preferably from about 90° C. to about 200° C., for a period of time sufficient to obtain a dry film. Generally this time will range from about one minute to about two hours. The components present in a particular crosslinkable polymeric coating composition will determine the temperature and time that will be required to obtain an adequate cure and a good coating film.

EXAMPLES

The following examples present illustrative embodiments of this invention and are not intended to limit its scope. All of the parts, percentages and proportions referred to herein, including the claims, are by weight unless otherwise indicated. The following terms used in the examples have the following meanings:

| Designation | Description |
| --- | --- |
| Photoinitiator I | Hexafluoroantimonate sulfonium salt, available as CYRACURE TM UVI-6974 from Union Carbide Chemicals and Plastics Company Inc. |
| Polyol I | Propylene oxide polyol with an average hydroxyl number of 112 and an average equivalent weight of 500, available as NIAX TM Polyol LHT-112 from Union Carbide Chemicals and Plastics Company Inc. |
| Polyol II | Trihydroxyl functional $\epsilon$-caprolactone polyol with an average hydroxyl number of 312 and an average equivalent weight of 180, available as TONE TM -0305 from Union Carbide Chemicals and Plastics Company Inc. |
| Epoxide I | 3,4-Epoxycyclohexanemethyl 3,4-epoxycyclohexanecarboxylate, available as CYRACURE TM UVR-6110 from Union Carbide Chemicals and Plastics Company Inc. |
| Epoxide II | 1-Vinyl 3,4-epoxycyclohexane. |
| Surfactant I | A silicone-alkylene oxide copolymer, available as SILWET TM L-7604 from Union Carbide Chemicals and Plastics Company Inc. |

Measurements and test procedures used in the examples are as follows:

Solvent Resistance (Double Acetone Rubs)

A measure of the resistance of the cured film to attack by acetone in which a film coating surface was rubbed with an acetone-soaked cloth back and forth with hand pressure. A rub back and forth over the film coating surface with the acetone-soaked cheesecloth was designated as one "double acetone rub".

Pencil Hardness

Pencil leads of increasing hardness values were forced against the film coating surface in a precisely defined manner as described in ASTM D3363-74 until one pencil lead cut through the surface of the film coating. The surface hardness was considered as the hardest pencil grade which just failed to cut or mar the film coating surface. The pencil leads in order of softest to hardest were reported as follows: 6B, 5B, 4B, 3B, 2B, B, HB, F, H, H, 3H, 4H, 5H, 6H, 7H, 8H, and 9H.

Crosshatch Adhesion

A lattice pattern with ten cuts in each direction was made in the coating film to the substrate and pressure-sensitive adhesive tape (Scotch Brand 606) was applied over the scored/cut substrate and then quickly removed. The amount of coating remaining on the scored area is the "Percent Crosshatch Adhesion".

Gardner Impact Resistance

A measure of the ability of a cured film coating on a substrate to resist rupture from a falling weight. A Model IG-1120 Gardner Impact Tester equipped with an eight-pound dart was used to test film coatings cast and cured on steel panels. The dart was raised to a given height in inches and dropped onto either the coated side of the coated steeel panel (direct or forward impact resistance) or the uncoated side of the coated steel panel (reverse impact resistance). The height-of-drop in inches times weight of dart (8 pounds), designated as inch-pounds, absorbed by the film without repturing was recorded as the films direct or reverse impact resistance.

EXAMPLES 1-17
Cycloaddition

These examples describe reacting dienes with dienophilic (meth/eth)acrylates to produce unsaturated cycloaliphatic esters. Specific reactants, and amounts, are given in Table A, using the following procedures.

In Example 1, 100 ml of toluene solvent and 5 grams (0.037 mole) of anhydrous aluminum chloride catalyst were added to a three-necked, one-liter, round-bottom flask equipped with a water-cooled reflux condenser, thermometer, and addition funnel. The mixture was kept under a nitrogen blanket and the flask contents were stirred as the indicated amount of dienophilic ester given in Table A dissolved in 50 ml of toluene was added dropwise over a 30-minute period. This was followed by the dropwise addition of the indicated amount of diene given in Table A in 25 ml of toluene over a one-hour period. The reaction temperature was maintained at 30° C. by occasionally cooling the reaction flask with cold water. After an additional two hours of stirring, the reactor contents were poured, with stirring, onto a mixture of 200 ml of ice and 10 ml of concentrated hydrochloric acid. The organic layer was then separated from the water layer and washed successively with 100 ml portions of a 5% aqueous hydrochloric acid solution and water. The reaction was upscaled by a factor of 2.5 and carried out two additional times to produce a total of 1328 grams of crude product with the following composition: 1.4% diene, 69% toluene, and 29% product. The mixture was transferred to a three-liter, round-bottom flask equipped with a 20-tray Oldershaw column and a water-cooled automatic reflux head. Distillation under vacuum gave 381 grams of product (86% yield based on combining ratios of original reactants) with a 99% purity and a boiling point of 160° C. at 145 mm Hg. The low viscosity product had a pleasing fragrance, and was stored for future use.

In Examples 2-13, the procedures of Example 1 is followed except that the dienophiles and dienes indicated in Table A are used.

In Examples 14-15, 200 ml of toluene solvent and 10 grams (0.037 mole) of anhydrous aluminum chloride catalyst are added to a three-necked, two-liter, round-bottom flask equipped with a water-cooled reflux condenser, thermometer, and addition funnel. The mixture is kept under a nitrogen blanket, and the flask contents cooled to 0° C. and stirred as the indicated amount of dienophilic ester given in Table A dissolved in 100 ml of toluene is slowly added over a 45-minute period. This is followed by the slow addition of the indicated amount of diene given in Table A in 100 ml of toluene over a two-hour period. The reaction temperature is slowly increased to 25° C. by heating or cooling the reaction flask with cold water. After stirring for an additional four hours, the reactor contents are poured, with stirring, onto a mixture of 400 grams of ice and 20 ml of concentrated hydrochloric acid. The organic layer is then separated from the water layer and washed successively with 100 ml portions of a 5% aqueous hydrochloric acid solution and of water. The product layer is then stripped at 70° C. and aspirator vacuum to remove any low molecular weight volatiles and toluene.

In Example 16, the procedure of Example 2 is followed using the amounts of diene and dienophilic ester given in Table A except for the following variations. The mixture is instead cooled to −5° C. and the reaction temperature is slowly increased to 5° C. and held there for 30 minutes and then slowly increased to 10° C. and held there for 60 minutes. Temperature is maintained by occasionally cooling the reaction flask with cold water or heating with a heat gun if necessary. After stirring for an additional two hours, the product is isolated using the same procedure.

In Example 17, the procedure of Example 16 is followed using the amounts of diene and dienophilic ester given in Table A except for the following variations. The mixture is instead kept under a nitrogen blanket at 25° C. and the reaction temperature held at 25° C. for 3 hours and then slowly increased to 40° C. and held there for 60 minutes. The same procedure is followed to produce and isolate product except that 600 grams of ice are used.

TABLE A

| | | | Cycloaddition Reactions | | | | | | | | | | |
| | | | | | | | | Cycloaliphatic Ester[a] | | | | | |
| Ex. | Diene (gms, moles) | Dienophile (gms, moles) | n | x | $R_1$ | $R_2$ | $R_3$ | $R_4$ | $R_5$ | $R_6$ | $R_7$ | $R_8$ | $R_9$ | $R_{10}$ |
|---|---|---|---|---|---|---|---|---|---|---|---|---|---|---|
| 1 | Isoprene (34, 0.5) | Ethyl acrylate (44, 0.44) | 1 | 0 | H | H | H, $CH_3$ | $CH_3$, H | H | H | — | — | H | $-C_2H_5$ |
| 2 | 1,3-Butadiene (81, 1.5) | HEA[d] (116, 1) | 1 | 0 | H | H | H | H | H | H | — | — | H | $-CH_2CH_2OH$ |
| 3 | 1,3-Butadiene (81, 1.5) | HPA[e] (130, 1) | 1 | 0 | H | H | H | H | H | H | — | — | H | Note j |
| 4 | 1,3-Butadiene (81, 1.5) | HEMA[f] (130, 1) | 1 | 0 | H | H | H | H | H | H | — | — | $CH_3$ | $-CH_2CH_2OH$ |
| 5 | Isoprene (102, 1.5) | HPMA[g] (144, 1) | 1 | 0 | H | H | H, $CH_3$ | $CH_3$, H | H | H | — | — | $CH_3$ | Note j |
| 6 | 1,3-Butadiene (270, 5) | DPPA[h] (525, 1) | 5 | 0 | H | H | H | H | H | H | — | — | H | Note k |
| 7 | 1,3-Butadiene (216, 4) | DPPA[h] (525, 1) | 4 | 0 | H | H | H | H | H | H | — | — | H | Note l |
| 8 | 1,3-Butadiene (162, 3) | DPPA[h] (525, 1) | 3 | 0 | H | H | H | H | H | H | — | — | H | Note m |
| 9 | 1,3-Butadiene (108, 2) | DPPA[h] (525, 1) | 2 | 0 | H | H | H | H | H | H | — | — | H | Note n |
| 10 | 1,3-Butadiene (54, 1) | DPPA[h] (525, 1) | 1 | 0 | H | H | H | H | H | H | — | — | H | Note o |

TABLE A-continued

Cycloaddition Reactions

| Ex. | Diene (gms, moles) | Dienophile (gms, moles) | n | x | $R_1$ | $R_2$ | $R_3$ | $R_4$ | $R_5$ | $R_6$ | $R_7$ | $R_8$ | $R_9$ | $R_{10}$ |
|---|---|---|---|---|---|---|---|---|---|---|---|---|---|---|
| 11 | 1,3-Butadiene (27, 0.5) | DPPA[h] (525, 1) | 0.5 | 0 | H | H | H | H | H | H | — | — | H | Note p |
| 12 | 2,4-Hexadiene (41, 0.5) | Ethyl acrylate (44, 0.44) | 1 | 0 | $CH_3$ | H | H | H | H | $CH_3$ | — | — | H | —$C_2H_5$ |
| 13 | 1,3-Hexadiene (41, 0.5) | Ethyl acrylate (44, 0.44) | 1 | 0 | $C_2H_5$ | H | H | H | H | H | — | — | H | —$C_2H_5$ |
| 14 | 1,3-Butadiene (162, 3) | TMPTA[i] (296, 1) | 3 | 0 | H | H | H | H | H | H | — | — | H | Note q |
| 15 | Isoprene (238, 3.5) | TMPTA[i] (296, 1) | 3 | 0 | H | H | H, $CH_3$ | $CH_3$, H | H | H | — | — | H | Note q |
| 16 | Cyclo-$C_5$[b] (231, 3.5) | TMPTA[i] (296, 1) | 1-3 | 0 | — | H | H | H | H | — | H | H | H | Note r |
| 17 | Cyclo-$C_5$TMS[c] (484, 3.5) | TMPTA[i] (296, 1) | 1-3 | 0 | — | H | H | H | H | — | H | $Si(CH_3)_3$ | H | Note r |

Notes for Table A:

a - Having a structure as shown in FIG. 1 with the noted substituents.
b - Cyclo-$C_5$ = 1,3-cyclopentadiene
c - Cyclo-$C_5$TMS = 1,3-cyclopentadiene-5-yltrimethylsilane
d - HEA = hydroxyethyl acrylate
e - HPA = hydroxypropyl acrylate
f - HEMA = hydroxyethyl methacrylate
g - HPMA = hydroxypropyl methacrylate
h - DPPA = dipentaerythritol pentaacrylate
i - TMPTA = trimethylolpropane triacrylate
j - —$CH_2CH(CH_3)OH$
k - $[(-CH_2)_{aa}(HOCH_2)_{bb}(CH_2=CHCOOCH_2)_{cc}CCH_2]_2O$ wherein aa is 5, bb is 1 and cc is 0.
l - $[(-CH_2)_{aa}(HOCH_2)_{bb}(CH_2=CHCOOCH_2)_{cc}CCH_2]_2O$ wherein aa is 4, bb is 1 and cc is 1.
m - $[(-CH_2)_{aa}(HOCH_2)_{bb}(CH_2=CHCOOCH_2)_{cc}CCH_2]_2O$ wherein aa is 3, bb is 1 and cc is 2.
n - $[(-CH_2)_{aa}(HOCH_2)_{bb}(CH_2=CHCOOCH_2)_{cc}CCH_2]_2O$ wherein aa is 2, bb is 1 and cc is 3.
o - $[(-CH_2)_{aa}(HOCH_2)_{bb}(CH_2=CHCOOCH_2)_{cc}CCH_2]_2O$ wherein aa is 1, bb is 1 and cc is 4.
p - $[(-CH_2)_{aa}(HOCH_2)_{bb}(CH_2=CHCOOCH_2)_{cc}CCH_2]_2O$ wherein aa is 0.5, bb is 1 and cc is 4.5.
q - $(-CH_2)_3CCH_2CH_3$ r - 

EXAMPLES 18–40

Epoxidation and Other Derivatizations

These examples describe various reactions of unsaturated cycloaliphatic esters including epoxidation, hydrogenation, (trans)esterification, and other derivatizations. Specific reactants and amounts are given in Table B using the following procedures. In Examples 18, 19, 37, 38 and 47, unsaturated cycloaliphatic esters were epoxidized as shown in Equation VII. In Examples 20–35, 43–46, 55–57, 63–65, 73 and 75, unsaturated cyloaliphatic esters are epoxidized, as shown in Equation VII. In Examples 48–50 and 57–59, unsaturated cyloaliphatic esters are hydrogenated, as shown in Equation VIII. In Examples 69–71, unsaturated cyloaliphatic esters having active hydrogen are further esterified, as shown in Equation IX. In Example 74, unsaturated cyloaliphatic esters are transesterified, as shown in Equation VI. Other derivatizations are shown in Examples 39–42, 51–53, 60–62 and 66–68.

In Example 18, 50 ml of methylene chloride solvent and 36.6 grams (0.200 mole) of the Example 1 product were added to a three-necked, two-liter, round-bottom flask equipped with a water-cooled reflux condenser, thermometer, and dropping funnel. The compounds were well mixed. A solution containing 42 grams (0.243 mole) of meta-chloroperoxybenzoic acid epoxidizing agent and 800 ml of methylene chloride was prepared in a glass container. This solution was added to the reaction flask through the dropping funnel over a 65-minute period with stirring. The temperature was initially 25° C. and is 29° C. at the end of the addition. The solution temperature dropped to 25° C. over a 90-minute period. Then, the system was warmed to 40° C. and maintained at this temperature for 2.5 hour. Heating was discontinued and the reaction mass was allowed to stand under ambient conditions overnight (about 17 hours). The cured product was cooled by placing the reaction flask in an ice-water bath, and then filtered through a Buchner funnel to remove the meta-chlorobenzoic acid that formed during the epoxidation. The filtered methylene chloride containing the epoxide was then placed in a two-liter separatory funnel and washed with saturated sodium bicarbonate solution, with the pH of the organic layer and the neutralized bicarbonate analyzed until the organic layer was neutral. Then, the organic layer was washed with 50 ml of saturated, aqueous sodium chloride solution. The organic layer was dried over anhydrous magnesium sulfate for 45 minutes and filtered. The methylene chloride solvent was removed by simple distillation until the volume was about 100 ml. Chromatographic analysis of the product indicated that it contained 18.42% methylene chloride, 35% starting unsaturated ethyl ester, and 45.81% of a mixture of the corresponding epoxidized compounds, such as shown by Equation VII. The product was then vacuum distilled from a 200 ml round-bottom flask equipped with a 37 cm column packed with ⅛-inch glass helices. The fraction boiling at 126°–137°C. and 4 mm Hg pressure was collected as the desired epoxide mixture. Chromatographic analysis indicated the product was about 97% of the mixed epoxide isomer and 2.67% of the starting unsaturated ethyl ester.

In Example 19, an unsaturated cycloaliphitic ester was initially made using a 500 ml, round-bottom, glass reaction flask equipped with a stirrer, a temperature measuring device, and a 20-tray Oldershaw column and decanting head which was charged with 53 grams (0.42 moles) of 3-cyclohexene-1-carboxylic acid, 116 grams (2.5 moles) of absolute ethanol solvent, 100 ml of cyclohexane azeotroping solvent, and 0.30 grams of sodium hydrogen sulfate esterification catalyst. The stirred reaction mass was brought to reflux and the upper layer of the water/ethanol/cyclohexane azeotropic mixture was returned to the column. After a reaction time of 12 hours, chromatographic analysis indicated that the 3-cyclohexene-1-carboxylic acid had been quantitatively converted into the corresponding ethyl ester. The excess ethanol was then evaporated under a vacuum of 100 mm Hg. The reaction mixture was diluted with cyclohexane, 50 ml, and successively washed with 50 ml portions of a saturated sodium bicarbonate solution and water. The organic layer was dried over anhydrous magnesium sulfate and transferred to a 200 ml flask and distilled under vacuum through a 37 cm column packed with one-eighth-inch glass helices to yield 47 grams (73% yield) of the desired ethyl ester (b.p. 116°–118° C. at 100 mm Hg) with a purity exceeding 99%.

In Example 19, epoxidation was conducted using a 3-neck, 200 ml, glass round-bottom flask was equipped with a water-cooled reflux condenser, thermometer, and addition funnel and charged with 45 grams (0.29 mole) of the product of the designated examples. While stirring, 90 grams (0.29 mole) of a 25% solution of peracetic acid epoxidizing agent in ethyl acetate solvent was added dropwise to the reaction flask over a one-hour period. The reaction temperature was maintained below 80° C. by cooling the flask with cold water. After all the peracetic acid solution had been added, the reaction mass was stirred for an additional 30 minutes and then washed twice with 60 ml portions of water followed by two washes, 60 ml portions, with an aqueous saturated sodium bicarbonate solution. The organic layer was dried over anhydrous magnesium sulfate, filtered, and transferred to a 200 ml round-bottom flask. The product was distilled under vacuum through a 37 cm column packed with one-eighth inch glass helices to give 28 grams (57% yield) of ethyl 3,4-epoxycyclohexanecarboxylate, b.p. 87°–88° C. at 1.0 mm Hg, purity exceeding 99% was provided.

In Examples 20–35, the epoxidation procedure of Example 19 is followed except that the unsaturated esters identified in Table B are used.

Example 36 describes the preparation of 2-propoxyethyl 3-cyclohexenecarboxylate. A 500 ml, round-bottom flask equipped with a 10-tray Oldershaw column and decanting head, thermometer, and a connecting tube with stopcock was charged with 126 grams (1.0 mole) of 3-cyclohexene-1-carboxylic acid, 99 grams (0.95 mole) of 2-propoxyethanol, and 100 ml of toluene. The reaction mass was stirred and brought to reflux. Then 1.1 grams of titanium tetrabutoxide was added via the connecting tube. The temperature of the reaction mass was slowly increased to 200° C. and held at this temperature while removing water and solvent overhead. After a reaction time of 8 hours, the product was cooled and washed with 50 ml of dilute phosphoric acid (10 weight percent in water) and filtered to remove the titanium salts. The organic layer was separated from the water layer, and the organic layer was successively washed with 50 ml portions of a saturated sodium bicarbonate solution and with water. Distillation of the crude product under vacuum through a 12-cm Vigreux column gave 152 grams (75% yield) of 2-propoxyethyl 3-cyclohexenecarboxylate (b.p. 88°–90° C. at 2.0 mm Hg) with a chromatographically analyzed purity exceeding 98%.

In Example 37, butyl bis(3-cyclohezenecarboxylate) was made using the procedure described in Example 36 by reacting 124 grams (0.98 mole) of 3-cyclohexene-1-carboxylic acid with 43.2 grams (0.48 mole) of 1,4-butanediol. Distillation of the crude product resulted in a yield of 121 grams (83% yield) of butyl bis(3-cyclohezene carboxylate) (b.p. 223°–225° C. at 2.0 mm Hg) with an chromatographically analyzed purity exceeding 99%. The product was epoxidized by the same procedure used in Example 19. Chromatographic analysis indicated the corresponding diepoxide was obtained.

In Example 38 trimethylolpropane tris(3-cyclohexenecarboxylate) and the corresponding triepoxide were made. In the same manner as described in Example 36, 124 grams (0.98 mole) of 3-cyclohexenecarboxylic acid was reacted with 43 grams (0.32 mole) of trimethylolpropane (2-ethyl-2-hydroxymethyl)-1,3-propanediol. Purification of the crude product yielded 139 grams (95% yield) of trimethylolpropane tris(3-cyclohexenecarboxylate) in the form of a pale yellow, viscous liquid. A portion of the product was epoxidized by the same procedure as that used in Example 19, and chromatographic analysis indicated that the product was trimethylolpropane tris(3,4-cyclohexane carboxylate).

In Examples 39–42, 0.20 mole of the ester given in Table B are placed-in a glass reaction flask equipped with a stirrer, thermometer, nitrogen inlet and outlet, and an addition tube. The ester is heated to 60° C. and held at this temperature for one hour with stirring and while sparging with dry nitrogen. Then, 0.1 made of the designated diisocyanate is slowly added with stirring over a 30-minute period at the temperature of 60° C. The temperature is controlled between 55° C. and 65° C. by use of either an ice/water bath or a heating gun for a time period sufficient for the isocyanato groups to react with the hydroxyl groups on the ester. Completion of reaction is either determined by infrared analysis for residual isocyanate or by titration for free isocyanate.

In Examples 43–46, the products of Examples 39–42 are epoxidized by the same procedure as described in Example 31.

In Example 47, 140 grams (1.1 moles) of 3-cyclohexene-1-carboxylic acid were reacted with 46 grams (0.18 mole) of dipentaerythritol using the procedures as described in Example 36. Evaporation of the toluene and purification of the crude product gave 150 grams (92% yield) of the corresponding hexafunctional unsaturated product which was epoxidized following the procedure described in Example 19.

In Examples 48–71, unsaturated cyclohexene esters of Examples 2–4 are each alone or in combination reacted in either neat form or in a solvent diluted form to make derivative compounds. In Examples 48–50, the esters are hydrogenated to form saturated, monohydroxylfunctional compounds as shown in Equation VIII. In Examples 51–53, the esters are reacted with monoisocyanate, such as methyl isocyanate, butyl isocyanate or phenyl isocyanate, to form the corresponding unsaturated cyclohexene urethanes. The urethanes of Examples 51–53 are epoxidized in Examples 54–56 following the procedure described in Example 31 to form the corresponding cycloaliphatic epoxides and are hydrogenated in Examples 57–59 to form the corresponding saturated urethanes. In Examples 60–62, one mole of each ester is reacted with 1 to 50 moles of ethylene oxide, propylene oxide, butylene oxide, epichlorohydrin, or ε-caprolactone each alone or in combination to form the corresponding unsaturated cyclohexene adducts. In Examples 63-65, these adducts are epoxidized following the procedure described in Example 31. In Examples 66-68, the epoxides of Example 63-65 are reacted with monoisocyanates using the procedure as described in Example 51-53. In Examples 69-71, two moles of the adducts of Examples 60-62 are reacted with an anhydride and/or a carboxylic acid or polycarboxylic acid, such as maleic anhydride or acid, phthalic anhydride or acid, isophthalic anhydride, trimeletic anhydride, hexahydrophthalic anhydride, or other anhydride or carboxylic acid to form bis(cyclohexene) compounds that are linked by a maleate linkage in the case of maleic anhydride, or other linkage indicative of the specific acid or anhydride used.

In Example 72, transesterification is described for preparing other ester compounds, as shown in Equation VI. One mole of the product of Example 1, 2 moles of butanol (1.0 mole excess), and 0.5 weight percent tetrabutyltitanate transesterification catalyst, are placed in a suitable reaction flask equipped with a thermometer, stirrer, and condenser. The contents of the flask are heated to 160° to 200° C. and held at these temperatures for 2 to 20 hours. Ethanol and excess butanol are removed by distillation, and the corresponding butyl ester product is recovered by further distillation.

In Example 73, the butyl ester of Example 72 is epoxidized by the process described in Example 31.

Example 74, describes preparation of an octafunctional unsaturated compound. In the same manner as described in Example 36, 127 grams (1.0 mole) of 3-cyclobexene-1-carboxylic acid is reacted with 39.8 grams (0.125 mole) of tripentaerythritol. The resulting reaction product, tripentaerythritolocta(cyclohexenecarboxylate) is formed as a viscous compound.

In Example 75 the product of Example 74 epoxidized by the procedure described in Example 31.

TABLE B

| | | Derivatizations | | | | | |
|---|---|---|---|---|---|---|---|
| Ex. | Product | Derivatizing Agent | Starting Ester | Ex. | Product | Derivatizing Agent | Starting Ester |
| 18 | Epoxide | m-CPBA[a] | Ex. 1 | 47 | Epoxide | Peracetic acid | (in Ex. 47) |
| 19 | Epoxide | Peracetic acid | (in Ex. 19) | 48 | Hydrog. | Hydrogen | Ex. 2 |
| 20 | Epoxide | Peracetic acid | Ex. 2 | 49 | Hydrog. | Hydrogen | Ex. 3 |
| 21 | Epoxide | Peracetic acid | Ex. 3 | 50 | Hydrog. | Hydrogen | Ex. 4 |
| 22 | Epoxide | Peracetic acid | Ex. 4 | 51 | Urethane | Isocyanate | Ex. 2 |
| 23 | Epoxide | Peracetic acid | Ex. 5 | 52 | Urethane | Isocyanate | Ex. 3 |
| 24 | Epoxide | Peracetic acid | Ex. 6 | 53 | Urethane | Isocyanate | Ex. 4 |
| 25 | Epoxide | Peracetic acid | Ex. 7 | 54 | Epoxide | Peracetic Acid | Ex. 51 |
| 26 | Epoxide | Peracetic acid | Ex. 8 | 55 | Epoxide | Peracetic Acid | Ex. 52 |
| 27 | Epoxide | Peracetic acid | Ex. 9 | 56 | Epoxide | Peracetic Acid | Ex. 53 |
| 28 | Epoxide | Peracetic acid | Ex. 10 | 57 | Hydrog. | Hydrogen | Ex. 51 |
| 29 | Epoxide | Peracetic acid | Ex. 11 | 58 | Hydrog. | Hydrogen | Ex. 52 |
| 30 | Epoxide | Perpropionic acid | Ex. 12 | 59 | Hydrog. | Hydrogen | Ex. 53 |
| 31 | Epoxide | Peracetic acid | Ex. 13 | 60 | Ether | Epoxides | Ex. 2 |
| 32 | Epoxide | Peracetic acid | Ex. 14 | 61 | Ether | Epoxides | Ex. 3 |
| 33 | Epoxide | Peracetic acid | Ex. 15 | 62 | Ether | Epoxides | Ex. 4 |
| 34 | Epoxide | Peracetic acid | Ex. 16 | 63 | Epoxide | Peracetic acid | Ex. 60 |
| 35 | Epoxide | Peracetic acid | Ex. 17 | 64 | Epoxide | Peracetic acid | Ex. 61 |
| 36 | Ester | — | (in Ex. 36) | 65 | Epoxide | Peracetic acid | Ex. 62 |
| 37 | Epoxide | Peracetic acid | (in Ex. 47) | 66 | Urethane | Isocyanate | Ex. 63 |
| 38 | Epoxide | Peracetic acid | (in Ex. 38) | 67 | Urethane | Isocyanate | Ex. 64 |
| 39 | Urethane | IPDI[b] | Ex. 2 | 68 | Urethane | Isocyanate | Ex. 65 |
| 140 | Urethane | TDI[c] | Ex. 3 | 69 | (Di)ester | Acid/anhydride | Ex. 60 |
| 41 | Urethane | DPMDI[d] | Ex. 4 | 70 | (Di)ester | Acid/anhydride | Ex. 61 |
| 42 | Urethane | DCHMDI[e] | Ex. 5 | 71 | (Di)ester | Acid/anhydride | Ex. 62 |
| 43 | Epoxide | Peracetic acid | Ex. 39 | 72 | Transester | Butanol | Ex. 1 |
| 44 | Epoxide | Peracetic acid | Ex. 40 | 73 | Epoxide | Peracetic acid | Ex. 72 |
| 45 | Epoxide | Peracetic acid | Ex. 41 | 74 | Ester | — | (in Ex. 74) |
| 46 | Epoxide | Peracetic acid | Ex. 42 | 75 | Epoxide | Peracetic acid | Ex. 74 |

Notes for Table B
[a] m-CPBA = meta-chloroperoxybenzoic acid
[b] IPDI = isophorone diisocyanate
[c] TDI = toluene diisocyanate
[d] DPMDI = 4,4'-diphenylmethane diisocyanate
[e] DCHMPI = 4,4'-dicyclohexanemethyl diisocyanate

EXAMPLES 76-92

Coatings

These examples describe coating compositions containing expoxides of unsaturated cycloaliphatic esters produced in previous examples. In Examples 76-80, the ingredients listed in Table C were placed in ember-colored, glass bottles, mixed well, and coated onto Bonderite 37 steel panels with a No. 20 wire-wound rod. The coatings were cured by passing them under a 300 watt-/inch ultraviolet light source (Fusion Systems Type A lamp) at 10 feet per minute. One panel coated with each mixture was exposed to the ultraviolet light radiation and allowed to stand for 24 hour before testing. A second panel coated in the same manner was given a thermal post cure of 10 minutes at 100° C. after ultraviolet light exposure. The coatings were tested using the previously described test procedures with the results listed in Table D. After either ultraviolet light exposure alone or ultraviolet light exposure plus thermal post cure, the Example 76 coating remained tacky indicating that as would be expected, it probably had a glass transition temperature below room temperature. These examples demonstrate that the product of Example 18 was a reactive diluent for ultraviolet light curable coatings and other systems. When used in such coatings, it yielded properties that were comparable to or better than (impact resistance) those that were obtained with a known reactive diluent, 1-vinyl-3,4-epoxycyclohexane. Since the Example 18 product had a residual tackiness, it has a potential for use in certain adhesives.

In Examples 81-83, the ingredients listed in Table C were placed in amber bottles, well mixed, and coated onto Bonderite 37 steel panels with a No. 20 wire-wound rod. The coatings were cured with a 300 watt per inch ultraviolet light source (Fusion Systems Type A lamp) at 10 feet per minute. One set of coated panels was only exposed to the ultraviolet light source and then allowed to stand at room temperature for 24 hours before testing. A second set of coated panels was given a 10 minute, 100° C. thermal post cure after ultraviolet light exposure and then tested. Film thickness was 0.0008 inches (0.8 mil) for all samples tested.

In Examples 84-87, the ingredients listed in Table C were placed in glass bottles, well mixed, and coated onto Bonderite 37 steel panels with a No. 20 wire-wound rod. The coatings were cured with a 300 watt-per-inch ultraviolet light source, Fusion Systems Type V ultraviolet lamp) at 10 feet per minute. The resultant coatings had excellent adhesion and solvent resistance, were quite hard, and displayed good impact resistance when tested directly on the surface of the coating except for the coating of Example 86 which displayed a combination of high hardness and toughness with excellent impact resistance when tested both directly on the surface of the coated substrate and from the reverse side of the coated substrate.

In Examples 88-92, the ingredients listed in Table C were placed in glass bottles, well mixed, and coated onto Bonderite 37 steel panels with a No. 20 wire-wound rod. The coatings were cured with a 300 watt-per-inch ultraviolet light source, Fusion Systems Type V ultraviolet lamp) at 10 feet per minute. The resultant coatings were hard and had excellent adhesion and solvent resistance, and displayed good impact resistance when tested directly on the surface of the coating. The coating of Example 92 was not tested for impact resistance.

TABLE C

| | Cycloaliphatic Epoxide | | | | | |
|---|---|---|---|---|---|---|
| Ex. | Ex. | Amount | Epoxide | Polyol | Photoinitiator | Surfactant |
| 76 | 18 | 4.83 | — | — | 0.15(I) | 0.02(I) |
| 77 | 18 | 1.45 | 8.20(I) | — | 0.30(I) | 0.05(I) |
| 78 | 18 | 1.45 | 6.20(I) | 2.00(I) | 0.30(I) | 0.05(I) |
| 79 | — | — | 8.20(I) 1.45(II) | — | 0.30(I) | 0.05(I) |
| 80 | — | — | 6.20(I) 1.45(II) | 2.00(I) | 0.30(I) | 0.05(I) |
| 81 | 19 | 1.83 | — | — | 0.15(I) | 0.02(I) |
| 82 | 19 | 1.45 | 8.20(I) | — | 0.30(I) | 0.05(I) |
| 83 | 19 | 1.45 | 6.20(I) | 2.00(I) | 0.30(I) | 0.05(I) |
| 84 | 37 | 2.93 | — | — | 0.118(I) | — |
| 85 | 37 | 2.75 | 1.96(I) | — | 0.118(I) | — |
| 86 | 37 | 2.93 | — | 0.70(II) | 0.07(I) | 0.02(I) |
| 87 | 37 | 2.75 | 1.96(I) | 0.60(II) | 0.11(I) | 0.15(I) |
| 88 | 38 | 3.03 | — | — | 0.033(I) | 0.025(I) |
| 89 | 38 | 2.05 | 1.01(I) | — | 0.028(I) | 0.022(I) |
| 90 | 38 | 2.04 | 0.54(I) 0.50(II) | — | 0.08(I) | 0.024(I) |
| 91 | 38 | 0.695 | 0.042(II) | 0.072(II) | 0.008(I) | 0.006(I) |
| 92 | 38 19 | 0.286 0.217 | 0.076(I) 0.070(II) | — | 0.011(I) | 0.003(I) |

TABLE D

| | Coatings Analysis[a] | | | | |
|---|---|---|---|---|---|
| Coating Ex. | Double Acetone Rubs | Crosshatch Adhesion | Pencil Hardness | Gardner Impact Resistance Direct | Reverse |
| 76[b] | — | — | — | — | — |
| 77 | 100 | 92(75) | 2H | 15(25) | <5 |
| 78 | 93(100) | 100 | 2H | 75(100) | 15(20) |
| 79 | 100 | 92(98) | 2H | 25 | <5 |
| 80 | 100 | 100 | 2H | 75(50) | 25(50) |
| 81[c] | —(3) | —(90) | —(6B) | —(<5) | —(25) |
| 82 | >100 | 98(80) | 2H | <5 | 25 |
| 83 | >100 | 100 | F | 5(<5) | 50 |
| 84 | >100 | 100 | 3H | 75 | <5 |
| 85 | >100 | 100 | 3H | 50 | <5 |
| 86 | >100 | 100 | 2H | 275 | 250 |
| 87 | >100 | 100 | 3H | 75 | <5 |
| 88 | >100 | 100 | H | 25 | <5 |
| 89 | >100 | 100 | 4H | 50 | <5 |
| 90 | >100 | 100 | 4H | 50 | <5 |
| 91 | >100 | 100 | H | 50 | <5 |
| 92 | 45 | 100 | 3H | | |

[a]Different values obtained after thermal post curing are in parentheses.
[b]Sample is tacky and no properties were determined after ambient cure.
[c]Low values after thermal cure reflect the uncrosslinked nature of this coating. Low pencil hardness of baked coating is evidence that the glass transition temperature was below the test temperature.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

We claim:

1. A process for preparing a cycloaliphatic epoxide of the formula:

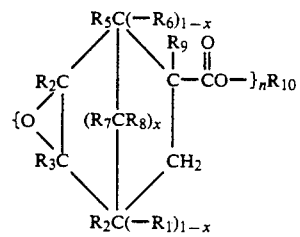

wherein:
n is at least 1;
$R_{1-8}$ are each, independently, hydrogen, $C_{1-10}$ hydrocarbyl with or without halo substitution, halo, cyano, or silyl;
$R_9$ is hydrogen, methyl, or ethyl;
$R_{10}$ is hydrocarbyl or oxyhydrocarbyl, provided $R_{10}$ has at least 5 carbon atoms or is oxyhydrocarbyl or is $-CH=CH_2$ when n is 1; and
x is 0 or 1;
which comprises:
reacting a diene of the formula:

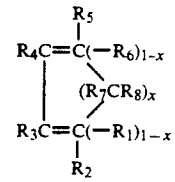

wherein $R_1$ to $R_8$ and x are as defined above, with a dienophilic (meth/eth)acrylate of the formula:

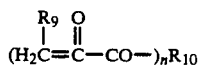

wherein $R_9 R_{10}$ and n are as defined above, to form an unsaturated cycloaliphatic ester;

transesterifying the unsaturated cycloaliphatic ester with an active hydrogen compound; and epoxidizing the transesterified unsaturated cycloaliphatic ester to form the cycloaliphatic epoxide.

2. The process of claim 1 wherein the active hydrogen compound is a hydroxyl-containing compound.

3. The process of claim 2, wherein the hydroxyl-containing compound is selected from the group consisting of alcohols, glycols and polyols.

4. The process of claim 1, wherein the diene is selected from 1,3-butadiene, isoprene, 1-3-dicyclopentadiene, and 1-3-cyclopentadien-5-yltrimethylsilane.

5. The process of claim 1, wherein the dienophilic (meth/eth)acrylate is selected from trimethylolpropane triacrylate and hydroxy acrylates.

* * * * *

UNITED STATES PATENT AND TRADEMARK OFFICE
CERTIFICATE OF CORRECTION

PATENT NO. : 5,268,489
DATED : December 7, 1993
INVENTOR(S) : Joseph V. Koleske et al It is certified that error appears in the above-identified patent and that said Letters Patent is hereby corrected as shown below:

Column 26, line 40, "$R_2C$" should read --$R_4C$--.

Signed and Sealed this

Twenty-sixth Day of April, 1994

Attest:

BRUCE LEHMAN

Attesting Officer          Commissioner of Patents and Trademarks